(12) United States Patent
Adhikari et al.

(10) Patent No.: US 10,376,844 B2
(45) Date of Patent: Aug. 13, 2019

(54) INTERFACE MODULE FOR FILTER INTEGRITY TESTING

(71) Applicant: EMD Millipore Corporation, Burlington, MA (US)

(72) Inventors: Jiwan Adhikari, Burlington, MA (US); John Erickson, Middleton, MA (US)

(73) Assignee: EMD Millipore Corp., Burlington, MA (US)

( * ) Notice: Subject to any disclaimer, the term of this patent is extended or adjusted under 35 U.S.C. 154(b) by 179 days.

(21) Appl. No.: 15/518,300

(22) PCT Filed: Dec. 2, 2015

(86) PCT No.: PCT/US2015/063305
§ 371 (c)(1),
(2) Date: Apr. 11, 2017

(87) PCT Pub. No.: WO2016/109084
PCT Pub. Date: Jul. 7, 2016

(65) Prior Publication Data
US 2017/0252703 A1    Sep. 7, 2017

Related U.S. Application Data

(60) Provisional application No. 62/098,724, filed on Dec. 31, 2014.

(51) Int. Cl.
*G01M 3/26* (2006.01)
*B01D 65/10* (2006.01)
*G01N 15/08* (2006.01)

(52) U.S. Cl.
CPC ........... *B01D 65/104* (2013.01); *B01D 65/10* (2013.01); *G01M 3/26* (2013.01); *G01N 15/082* (2013.01); *G01N 2015/084* (2013.01)

(58) Field of Classification Search
CPC .. B01D 29/603; B01D 65/102; B01D 65/104; G01N 2015/084
See application file for complete search history.

(56) References Cited

U.S. PATENT DOCUMENTS

RE31,952 E * 7/1985 Wilcox ............. B01D 46/0004
239/514
4,711,267 A * 12/1987 Schwelm ............. F15B 11/006
137/596.15

(Continued)

FOREIGN PATENT DOCUMENTS

DE    102010008524 A1 * 8/2011 ........... B01D 29/114
FR    2145858 A5 * 2/1973 ............... F16K 11/22

(Continued)

OTHER PUBLICATIONS

Millipore, "Exact-Air Integrity Tester—Automatic Water-Based Integrity Test Unit for Hydrophobic Vent Filters", Nov. 1999, 4 pages.

(Continued)

*Primary Examiner* — David A Rogers
(74) *Attorney, Agent, or Firm* — Eric J. Martineau

(57) ABSTRACT

A testing apparatus employs an interface module removably attached to a filter testing device. The interface module includes a first flowpath communicating with an outlet of the testing device and a housing of the filter device, a first valve disposed in the first flowpath, a second flowpath communicating with the housing of the filter device and an exhaust, a second valve disposed in the second flowpath, and an enclosure enclosing the first flowpath, the first valve, the second flowpath, and the second valve. The interface module is cleanable and/or sterilizable, and replaceable. A filter integrity testing method uses an interface module to prevent contamination of the testing device and cross-contamination of different filter devices and avoid liquid ingress into the testing device.

19 Claims, 2 Drawing Sheets

(56) References Cited

U.S. PATENT DOCUMENTS

| | | | |
|---|---|---|---|
| 5,282,380 A | 2/1994 | DiLeo et al. | |
| 5,353,630 A * | 10/1994 | Soda | B01D 65/102 |
| | | | 73/38 |
| 5,417,101 A * | 5/1995 | Weich | B01D 29/114 |
| | | | 73/38 |
| 5,457,986 A | 10/1995 | DiLeo et al. | |
| 5,507,959 A | 4/1996 | Glick | |
| 5,570,959 A | 11/1996 | Moriwaki et al. | |
| 5,627,328 A * | 5/1997 | Sheridan | G01N 1/2258 |
| | | | 73/863.83 |
| 5,786,528 A | 7/1998 | DiLeo et al. | |
| 7,587,927 B2 | 9/2009 | Burke et al. | |
| 8,084,259 B2 | 12/2011 | DiLeo | |
| 8,117,886 B2 * | 2/2012 | Rolff | G01M 3/207 |
| | | | 73/1.02 |
| 8,518,166 B2 * | 8/2013 | Tasi | B01D 46/0086 |
| | | | 55/385.2 |
| 8,800,600 B2 * | 8/2014 | Huang | F15B 13/043 |
| | | | 137/596.14 |
| 9,121,622 B2 * | 9/2015 | Dobbyn | B08B 15/023 |
| 9,255,917 B2 * | 2/2016 | Miyai | G01N 33/0006 |
| 9,377,331 B2 * | 6/2016 | Erta Carrera | G01F 1/00 |
| 9,476,790 B2 * | 10/2016 | Kajikawa | G01L 27/005 |
| 9,726,591 B2 * | 8/2017 | Helle | B01D 65/102 |
| 2003/0075920 A1 * | 4/2003 | Eriksson | F15B 13/0817 |
| | | | 285/126.1 |
| 2006/0027275 A1 * | 2/2006 | Eriksson | F15B 13/0817 |
| | | | 137/884 |
| 2010/0154513 A1 * | 6/2010 | Lin | B01D 46/42 |
| | | | 73/38 |
| 2011/0121946 A1 * | 5/2011 | Burke | B01D 29/52 |
| | | | 340/10.1 |
| 2011/0297251 A1 * | 12/2011 | Huang | F15B 13/0835 |
| | | | 137/485 |
| 2012/0059603 A1 | 3/2012 | Stering | |
| 2013/0068329 A1 * | 3/2013 | Klaphake | F15B 13/0842 |
| | | | 137/625.12 |
| 2015/0059584 A1 * | 3/2015 | Steins | B01D 46/0005 |
| | | | 96/417 |
| 2015/0316462 A1 * | 11/2015 | Helle | B01D 65/102 |
| | | | 222/1 |

FOREIGN PATENT DOCUMENTS

| | | |
|---|---|---|
| GB | 2132366 A | 7/1984 |
| JP | 04-348252 A | 12/1992 |
| JP | 10-225628 A | 8/1998 |
| WO | 98/35749 A1 | 8/1998 |
| WO | 2016/109230 A2 | 7/2016 |

OTHER PUBLICATIONS

International Search Report and Written Opinion received for PCT Patent Application No. PCT/US2015/063305, dated Mar. 16, 2016, 12 pages.

* cited by examiner

INTERFACE MODULE FOR FILTER INTEGRITY TESTING

TECHNICAL FIELD

Embodiments of this disclosure relate generally to integrity testing of filter devices. In particular, various embodiments of an interface module, a testing apparatus including the interface module, and a method of testing the integrity of filter devices using the interface module are described.

BACKGROUND

Filtration devices and methods are known and used in a variety of industries, including pharmaceutical, biotechnology, food processing and packaging, oil and gas industries etc. For example, membrane filtration devices have been used to eliminate undesirable impurities and other potentially harmful contaminants from end products in pharmaceutical and biotechnology industries.

To ensure that filtration devices comply with desired performance criteria, the integrity of the filtration devices is routinely tested before and/or after use. Integrity testing determines if a filtration device is free of defects or breaches in the membrane or porous material of the filtration device exceeding a desired size limitation, which would impair the device function and thus allow the end product to become contaminated with harmful or undesirable materials.

Integrity testing of filtration devices can be destructive or non-destructive. Destructive test is typically performed as a lot release criteria on samples from manufacturing lots of fabricated filter products. In a destructive test, a filter product is challenged with bacteria to determine the filter's ability to retain the bacteria. The test is "destructive" because it renders the filter unusable for actual application. Non-destructive test is routinely conducted on each filter device before and after use. The stringent requirements of the pharmaceutical industry dictate that non-destructive tests on filter devices must be performed in each sterilizing application at the point of use and immediately post use.

Various non-destructive testing methods have been developed, including the bubble point test, diffusion test, water intrusion test, and their variations. In conventional non-destructive testing methods, the testing equipment is susceptible to undesirable exposure to various contaminants including hazardous substances, particulates, liquids, and/or biological components. In general, at the beginning of an integrity test, a pressurized gas flows from the testing equipment to the filter device to be tested. At the end of the test, the system is de-energized and a significant amount of venting gas may flow in the direction to the testing equipment, exposing the testing equipment to the risk of contamination. The venting gas may contain residues of the wetting fluid and/or the product if the test is performed after filtration.

Integrity testing instruments are sensitive instruments and contamination of the instruments may disturb the accuracy of measurement. Further, contamination of the testing instruments can be a source of cross-contamination of different filter devices. Therefore, there is a need for apparatuses and methods that can protect the testing instruments from contamination and prevent cross-contamination. There is a general need for apparatuses and methods that can overcome the disadvantages of conventional filter integrity testing.

SUMMARY

Embodiments of a modular device for interfacing a filter integrity testing device are described. Also described are embodiments of an apparatus including an interface module and of a method for testing the integrity of filter devices.

Other embodiments are described further herein.

BRIEF DESCRIPTION OF THE DRAWINGS

These and various other features and advantages of the disclosure will become better understood upon reading of the following detailed description in conjunction with the accompanying drawings and the appended claims provided below, where:

DETAILED DESCRIPTION

Figure 1:
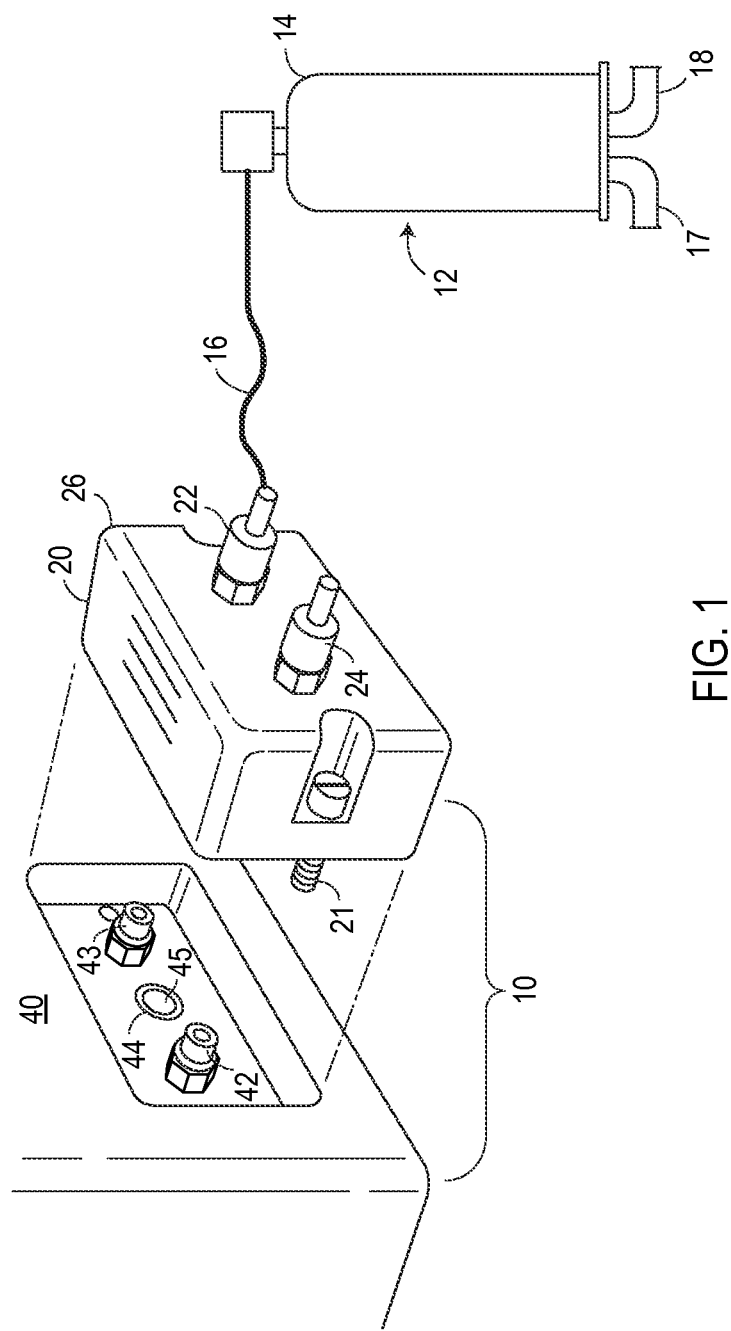
FIG. 1 schematically shows a testing apparatus in an arrangement for testing a filter device according to some embodiments of the disclosure.

Various embodiments of a modular device and an apparatus including an interface module are described. It is to be understood that the disclosure is not limited to the particular embodiments described as such may, of course, vary. An aspect described in conjunction with a particular embodiment is not necessarily limited to that embodiment and can be practiced in any other embodiments.

As used herein, when introducing elements of various embodiments, articles "a," "an," and "the" are intended to mean that there are one or more of the elements. The term "or" refers to a nonexclusive "or" unless the context clearly dictates otherwise. In the following description, well known components or steps may not be described in detail in order to avoid unnecessarily obscuring the embodiments of the disclosure.

As used herein, the term "module" or "modular device" refers to a separable unit that can be attached to and detached from a filter testing device. The unit is replaceable or exchangeable with other units identically or similarly constructed.

As used herein, the phrase "filter device" or "filter" refers to a device that includes a porous material capable of excluding or retaining specific solutes or suspended solids in a fluid based on the size of the solutes or solids. The filter device may include a housing enclosing the porous material. Alternatively, a housing may be specially designed for integrity testing of the filter device. The filter device may be in any suitable form, including a cartridge, a cassette, a cylinder, a column, a tube, a sheet, a chip, and so on. The porous material may comprise organic or inorganic compounds or a combination of organic and inorganic compounds. The porous material may be hydrophilic, hydrophobic, oleophobic, oleophilic or any combination thereof. The porous material may comprise one or more polymers or copolymers. The polymers may be crosslinked. The porous material can be configured for microfiltration, ultrafiltration and reverse osmosis. U.S. Pat. No. 7,587,927 to the present assignee describes various porous materials and filter devices comprising the porous materials. The disclosure of U.S. Pat. No. 7,587,927 is incorporated herein by reference.

As used herein, the phrase "filter integrity testing device," "filter testing device" or "testing device" refers to a device capable of testing the integrity and/or other characteristics of a filter device, including noting presence or absence of a defect or defects and/or determining the diameter of the pores of the porous material and pore size distribution. Integrity testing provides a means for ensuring that a particular filter device meets its desired performance criteria.

By way of example, integrity testing determines if a filter device is free of defects or breaches in the membrane or porous material of the filtration device exceeding a desired size limitation, which would impair the device function and thus allow the end product to become contaminated with harmful or undesirable material. Various testing devices are known and commercially available, including those based on the bubble point test, diffusion test, water intrusion test, and their variations. It should be noted that the principle and embodiments described in this disclosure are not limited to a specific type of testing device; rather, they can be implemented in any suitable testing devices. U.S. Pat. Nos. 5,282,380, 5,786,528, 7,587,927, and 8,084,259 to the present assignee describe various filter testing devices, the disclosures of all of which are incorporated herein by reference.

As used herein, the term "removable" refers to an embodiment of the modular device of this disclosure that the modular device is normally a part of a testing apparatus and can optionally be removed for cleaning and/or sterilizing, or for replacement.

As used herein, the term "cleanable" refers to an embodiment of the modular device of this disclosure that the modular device or its components can be cleaned using a suitable method such as wiping, flushing, and wet cleaning with a suitable cleaning agent.

As used herein, the term "sterilizable" refers to an embodiment of the modular device of this disclosure that the modular device or its components can be sterilized by e.g. subjecting the device or its components to high pressure steam in an autoclave for a period of time.

A modular device is provided. The modular device may include a first flowpath, a first valve disposed in the first flowpath, a second flowpath, and a second valve disposed in the second flowpath. The first flowpath, the first valve, the second flowpath, and the second valve may be enclosed in an enclosure.

The first flowpath is configured to communicate with an outlet of a testing device and a housing of a filter device. A pressurized gas may be introduced from the testing device to the housing of the filter device via the first flowpath with the first valve open. The second flowpath is configured to communicate with the housing of the filter device and an exhaust. The pressurized gas or at least a portion of the pressurized gas in the housing of the filter device may be vented via the second flowpath with the second valve open.

The modular device may be removably attached to a testing device and pneumatically connected to the housing of the filter device. The modular device or its parts, including the first and second flowpaths, the first and second valves, and the enclosure, may be cleanable and/or sterilizable. Therefore, after an integrity test, the modular device may be disconnected with the filter device and detached from the testing device for cleaning and/or sterilization. The proper cleaning and/or sterilization of the modular device can prevent cross-contamination in testing different filter devices. Alternatively, the modular device may be disposable or replaceable with other units identically or similarly constructed.

In some embodiments, the first flowpath may include a vertical section between the filter device and the first valve. The vertical section may prevent liquid ingress from the filter housing to the testing device. In some embodiments, the modular device may further include a check valve disposed in the first flowpath. The check valve may be configured to prevent a liquid flow in a direction from the filter device to the testing device. In some embodiments, the check valve may be arranged in a vertical section of the first flowpath. Therefore, the use of the modular device may protect the testing device from contamination by preventing liquid ingress from the filter housing into the testing device.

In another aspect of the disclosure, an apparatus including a testing device and an interface module is provided. The interface module functions to interface the testing device with a filter device to be tested. A pressurized gas may be introduced from the testing device to the housing of the filter device via the interface module. The pressurized gas or at least a portion of the pressurized gas in the housing of the filter device may be vented to an exhaust via the interface module. The interface module can be removably attached to the testing device. Alternatively, the interface module can be attached to the housing of the filter device by means of an extension fitting connected to the testing device. The interface module is cleanable and/or sterilizable, or replaceable. The use of the interface module can protect the testing device from contamination by preventing liquid ingress from the filter housing to the testing device. The proper cleaning and/or sterilization of the interface module can prevent cross-contamination from batch to batch or product to product.

The interface module may include a first flowpath and a first valve disposed in the first flowpath. The first flowpath is configured to communicate with an outlet of the testing device and the housing of the filter device. A pressurized gas may be introduced from the testing device to the housing of the filter device via the first flowpath with the first valve open. The first flowpath may include a vertical section between the filter device and the first valve. The vertical section may prevent liquid ingress from the filter device to the testing device. In some embodiments, a check valve may be disposed in the first flowpath. The check valve may be configured to prevent a liquid flow in a direction from the filter device to the testing device.

The interface module may include a second flowpath and a second valve disposed in the second flowpath. The second flowpath is configured to communicate with the housing of the filter device and an exhaust. The pressurized gas or a portion of the pressurized gas in housing of the filter device may be vented to the exhaust via the second flowpath with the second valve open.

The first flowpath, the first valve, the second flowpath, and the second valve may be enclosed in an enclosure. The interface module may be pneumatically connected to the housing of the filter device via an elongate tube, and as such, nothing heavy would be placed on the top of the filter device. The interface module may also include proper fittings such as nuts, bolts, or the like for removable attachment to the testing device. Upon completion of an integrity test, the interface module may be disconnected with the filter device and detached from the testing device for cleaning and/or sterilization. The cleaned and/or sterilized interface module may be reused for testing different filter devices.

The testing device on which the interface module is attached to may be any suitable filter integrity testing device commercially available. By way of example, the testing device may be constructed or configured for non-destructive tests including the bubble point test, diffusion test, water intrusion test, and theirs variants, including the pressure hold test, pressure drop test, or pressure decay test, and the like Various testing devices are known and their detailed description is omitted herein to avoid obscuring the description of embodiments of this disclosure. In general, the testing device may include an inlet communicating with an external pressurized gas source and an outlet communicating with the filter device. In performing various non-destructive tests, a filter device may be pressurized at the beginning of the test. The pressurization is typically achieved by feeding the filter device with a compressed gas from the testing device, which is supplied with a pressurized gas from an external gas source. For some testing procedures, the testing device may include an internal gas tank having a reference volume for system sizing. The internal gas tank may communicate with the external gas source via the inlet of the testing device and communicate with the filter device via the outlet of the testing device.

The testing device may include various valves for controlling e.g. gas intake from the external pressurized gas source to the internal gas tank, from the internal gas tank to the outlet of the device, and for controlling venting of the testing device etc. For some testing procedures, the testing device may include an isolation valve for pressure decay measurement of the filter device during testing.

The testing device may include one or more pressure sensors or transducers for monitoring the pressure in the testing device, the filter device, or the internal gas tank. Apart from measuring the test pressure for filter testing, the testing device may have provisions for measuring the housing pressure before pressurizing the housing and during the test ending cycle to ensure that liquid ingress into the testing device is prevented. The testing device may also include one or more temperature sensors for monitoring the temperature e.g. in the internal gas tank.

The testing device may include a controller which may comprise a microprocessor and a memory unit. The controller may be configured to control and driving various valves coupled to the controller. The controller may be configured to detect pressure and temperature by monitoring various sensors coupled to the controller. An analog to digital converter may be included for converting analog signals to digital signals. The controller may be configured to store one or more sets of parameters for test procedures for one or more filter devices, including e.g. the critical pressure, the test pressure, the test time etc. The sets of parameters may be tailored to particular types of filter devices based on e.g. the chemical composition and pore size of the porous material etc.

The testing device may include a user interface to allow a user to interact with the testing device. The user interface may include an input device such as keypad, touch screen or the like to allow the user to enter instructions for a test procedure, and a display for displaying test results and/or other information relating to the test. The testing device may be configured for automatic integrity testing. Alternatively, the testing device may be configured for manual testing.

In a further aspect of the disclosure, a method of testing a filter device is provided. According to the method, a testing device is connected with a filter device via an interface module. The interface module may include a first flowpath communicating with an outlet of the testing device and a housing of the filter device, a first valve in the first flowpath, a second flowpath communicating with the housing of the filter device and an exhaust, a second valve in the second flowpath, and an enclosure enclosing the first flowpath, the first valve, the second flowpath, and the second valve.

After the testing device is connected with the filter device via the interface module, an integrity test can be conducted on the filter device. During the integrity test, a pressurized gas may be introduced to the housing of the filter device from the testing device via the first flowpath of the interface module with the first valve open. After the integrity test is completed, the pressurized gas or at least a portion of the pressurized gas in the housing of the filter device may be vented to the exhaust via the second flowpath of the interface module with the second valve open. The exhaust and the interface module may be located in the same classification area or different classification areas by using an elongate tube.

After the integrity test and depressurization of the filter device, the interface module may be disconnected with the filter device and detached from the testing device for cleaning and/or sterilization. The detached interface module may be then cleaned and/or sterilized, and reused in testing different filter devices.

The disclosed method can be implemented in any suitable filter integrity tests, including various non-destructive tests such as the bubble point test, diffusion test, and water intrusion test, pressure hold test, pressure drop test, and pressure decay test.

The bubble point test is based on the fact that the liquid, which spontaneously wets the porous material, is held in the pores by surface tension and capillary forces, and subsequent attempts to displace the wetting liquid with a gas require that the gas pressure be elevated to some critical level dependent on the size of pores or the size of defects if present in order to overcome the surface tension and capillary forces. The critical pressure required to force the liquid out of the pores, defined as the bubble point pressure, is a measure of the pore diameter as illustrated in the following equation:

$$\text{Bubble point } P = \frac{4k \cos \theta}{d} \sigma$$

where P represents the bubble point pressure; k is the pore shape correction factor; $\theta$ is the liquid-solid contact angle; $\sigma$ is the surface tension of the fluid; and d is the diameter of the largest pore. Therefore, at a certain level of pressure applied from the upstream side, liquid may be forced first from the set of largest pores, in keeping with the inverse relationship of the applied air pressure (P) and the diameter of the pore (d) as described in the above equation. When the wetting fluid is expelled from the largest pores, a bulk gas flow can be detected on the downstream side of the filter system. The bubble point measurement can determine the pore size of the filter membrane and if the filter is integral.

In a bubble point test procedure, the filter is wetted with an appropriate fluid, typically water for hydrophilic membranes or an alcohol/water mixture for hydrophobic membranes. The filter system is pressurized from the upstream side to e.g. about 80% of the expected bubble point pressure. The pressure is gradually increased in increments until rapid continuous bubbling is observed at the downstream side. The pressure at which the bubbles first appear is called the visual bubble point pressure of the sample. A visual bubble point pressure lower than the minimum allowable bubble point specified by the filter manufacturer can be an indication that the filter is non-integral.

The diffusion test is based on the fact that at a differential gas pressure below the bubble point, gas molecules migrate through the water-filled pores of a wetted membrane following Fick's Law of Diffusion.

$$N = \frac{DH \Delta P}{L}$$

where N is the permeation rate (moles of gas per unit time); D is the diffusivity of the gas in the liquid; H is the solubility coefficient of the gas; L is the thickness of liquid in the membrane (equal to the membrane thickness if the membrane pores are completely filled with liquid); and ΔP is the differential pressure between the upstream and downstream sides of the filter. Therefore, the permeation rate or gas diffusion flow rate of a filter is proportional to the differential pressure. At a test pressure e.g. about 80% of the minimum bubble point specified by the filter manufacturer, the gas which diffuses through the membrane is measured to determine a filter's integrity.

In a diffusion test procedure, the filter is thoroughly wetted with appropriate test fluid, typically water for hydrophilic membranes or an alcohol/water mixture for hydrophobic membranes. The pressure on the upstream side of the filter is slowly increased to the test pressure, typically at least 80% of the minimum allowable bubble point specified by the filter manufacturer. Once the system equilibrates, the gas flow at the downstream side is measured. A diffusion flow reading higher than the rate specified by the filter manufacturer can be an indication that the membrane is non-integral.

The pressure hold test, also known as pressure decay test or pressure drop test, is a variation of the diffusion test. In this test, the upstream pressure changes due to gas diffusion through the filter are measured. Because there is no need to measure gas flow downstream of the filter, the risk to downstream sterility is eliminated.

The water intrusion test, also known as water flow test, is particularly suitable for hydrophobic filters. The water intrusion test is based on the fact that liquid is repelled by the pores of hydrophobic filters by surface tension and capillary forces. The minimum pressure required to force liquid into the largest pores is called the water intrusion pressure. The intrusion pressure, which is a filter property analogous to the bubble point pressure, is inversely related to the pore size and used to indicate the relative pore size of various membranes and can be correlated to determine retention efficacy. The intrusion pressure (P) can be expressed by the following equation:

$$\text{Intrusion pressure } P = -\left[\frac{4k\cos\theta}{d}\sigma\right]$$

where the variables of the pore shape correction factor (k), the liquid-solid contact angle (θ), the surface tension of the fluid (σ), and the diameter of the largest pore (d) are the same as defined in the bubble test Equation described above. The negative sign (−) in the Equation results from the fact the contact angle of water on a hydrophobic solid is greater than 90 degree and thus the cosine of this angle is negative.

In a water intrusion test procedure, the upstream side of the hydrophobic filter cartridge housing is flooded with water. A pressurized air or nitrogen gas is then applied to the upstream side of the filter housing above the water level to a defined test pressure. A period of pressure stabilization takes place over a timeframe, during which the cartridge pleats adjust their positions under imposed pressures. After the system stabilizes, the test time starts. Any further pressure drop in the upstream pressurized gas volume signifies a beginning of water intrusion into the largest hydrophobic pores. In a water flow test for pleated membrane cartridge, an observed low flowrate is predominantly indicative of pleat compaction only, and thus of an integral filter. On the other hand, a large flowrate is predominantly indicative of water flowing through undesirably large pores signifying a defect which is intruded at the test pressure. U.S. Pat. Nos. 5,282,380, 5,457,986, 5,786,528, 7,587,927, and 8,084,259, describe various methods for determining filter integrity and pore size distribution, the disclosures of all of which are incorporated herein by reference.

Exemplary embodiments of an interface module and a method for testing the integrity of filter devices will now be described with reference to the figures. It should be noted that some figures are not necessarily drawn to scale. The figures are only intended to facilitate the description of specific embodiments, and are not intended as an exhaustive description or as a limitation on the scope of the disclosure. Further, it should be understood that while embodiments of an interface module is shown and described in conjunction with a testing device for illustration purpose, the principle and embodiments of this disclosure are not so limited. The interface module provided by the disclosure is cleanable and/or sterilizable, or replaceable, and can be removably attached to an instrument for interfacing with a device to be tested and detached from the instrument for cleaning, sterilization, or replacement. Indeed, these and other novel features of the interface module provided by this disclosure can be used with any kind of instrument that has components sensitive to water intrusion e.g. corrosion or the like. By way of example, the interface module of this disclosure is also useful in protecting flow meters used in some instruments.

FIG. 1 schematically shows an apparatus 10 in an arrangement for integrity testing a filter device 12 according to some embodiments of the disclosure. In general, the apparatus 10 includes a testing device 40 and an interface module 20, which can be removably attached to the testing device 40 via proper fittings 21. The filter device 12 to be tested may include a housing 14 and a porous material such as a membrane filter (not shown) contained in the housing 14. Alternatively, the housing 14 may be specially designed for integrity testing of a filter device. The filter device 12 may further include a fluid inlet 17 and a fluid outlet 18.

The interface module 20 may include a housing outlet 22 and an exhaust outlet 24. The housing outlet 22 can be pneumatically connected to the housing 14 of the filter device 12 via an elongate tube 16. The exhaust outlet 24 can be connected to an exhaust (not shown), which may be located in the same classification area with the apparatus 10 or in a different classification area by using an elongate tube. The interface module 20 further includes an inlet (not shown in FIG. 1) communicating with an outlet 45 of the testing device 40.

The testing device 40 can be any suitable testing device described above. By way of example, the testing device 40 may have a design or construction configured for one or more non-destructive tests, including the bubble point test, diffusion test, water intrusion test, and their variations. As shown, O-ring fittings 42 and 43 may be provided for removable attachment of the interface module 20 to the testing device 40. It should be appreciated that other alternative fittings known in the art can be used. Seals such as an O-ring face seal 44 can be used to provide proper sealing between the outlet 45 of the testing device 40 and the inlet (not shown) of the interface module 20.

Figure 2:
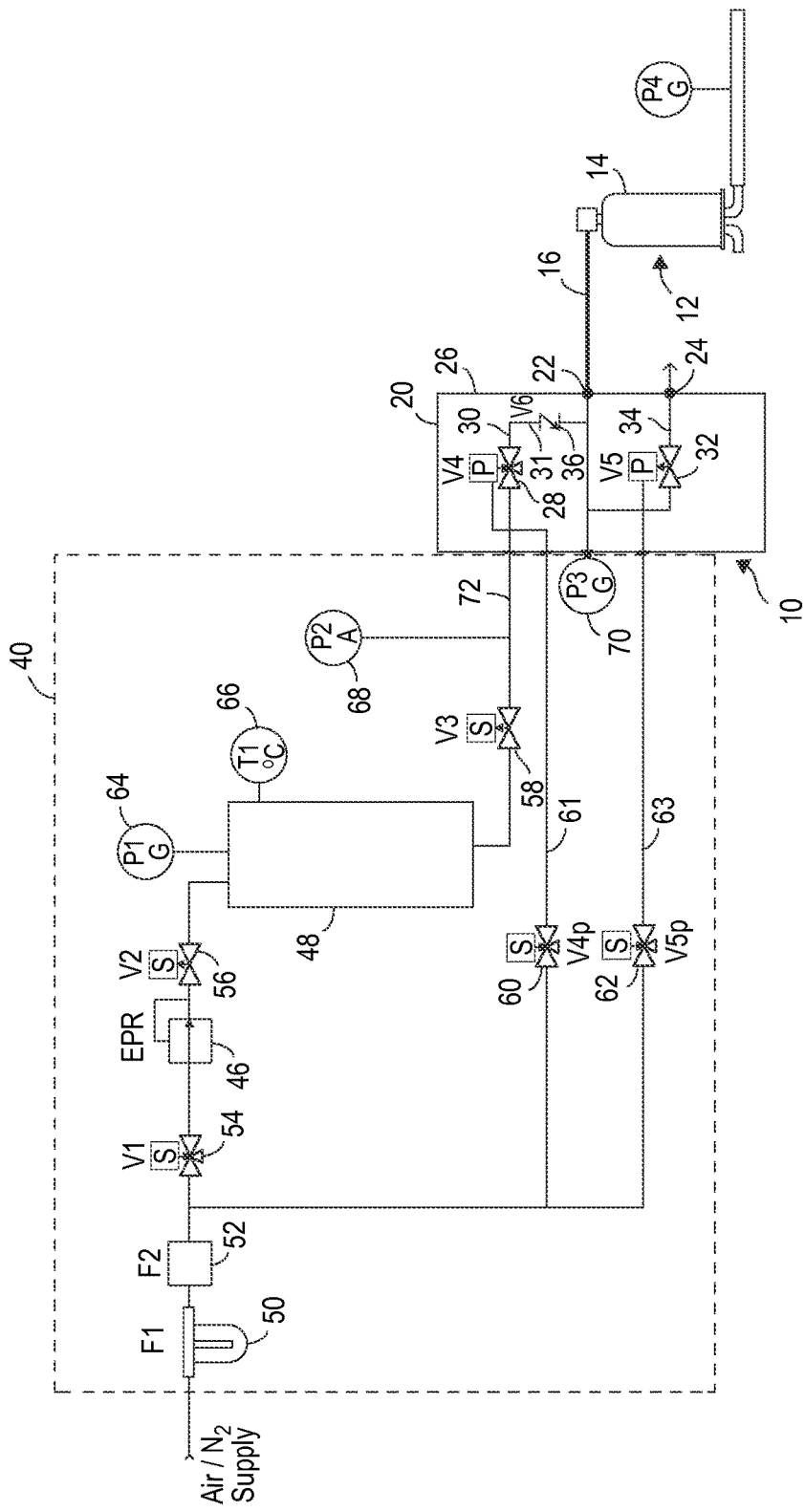
FIG. 2 is a diagram showing some details of a testing apparatus according to some embodiments of the disclosure.

Referring to FIG. 2, an exemplary testing device 40 includes, among other things not shown, an electronic pressure regulator 46, an internal gas tank 48, and filters 50 and 52. The pressure regulator 46 may be constructed or configured to regulate or set the value of the pressure in the internal gas tank 48. The internal gas tank 48 may have a calibrated volume and may be used for sizing or dampening a measurement gas used in the test. Filter 50 and 52 may be constructed or configured to remove moisture and/or large particles in the external pressurized gas supplied to the testing device 40.

The testing device 40 may include a supply valve 54, an inlet valve 56, and an isolation valve 58 on the flowpaths leading to or from the internal gas tank 48. The supply valve 54 may be arranged between the external gas supply source and the pressure regulator 46 and operate to supply a pressurized gas to the testing device 40. The inlet valve 56 may be arranged between the internal gas tank 48 and the pressure regulator 46 for regulating the pressure in the internal gas tank 48. The isolation valve 58 may be arranged between the internal gas tank 48 and the filter device 12 and operate to measure the pressure decay in the filter device during testing in some testing procedures. The testing device 40 may also include an outlet pilot valve 60 and an exhaust pilot valve 62 for controlling the outlet valve 28 and the exhaust valve 32 in the interface module 20 as will be described in greater detail below. One or more of the supply valve 54, inlet valve 56, isolation valve 58, and outlet and exhaust pilot valves 60 and 62 may be a solenoid valve, or a valve controlled by an electric current through a solenoid. Other types of valves known in the art can alternatively be used.

The testing device 40 may include a pressure sensor or transducer 64 for measuring the pressure in the internal gas tank 48, and a temperature sensor 66 for measuring the temperature in the internal gas tank 48. Pressure transducers 68 and 70 may be provided to measure the pressure in the testing device 40 and in the housing 14 of the filter device 12.

The testing device 40 may also include other known components, including such as a computer processor, a memory, a display, a printer, and other electronics, etc. These and other known components are not shown in FIGS. 1 and 2 and their detailed description is omitted in order to avoid unnecessarily obscuring the description of embodiments of this disclosure. The testing device 40 may be constructed for either manual or automatic integrity testing.

Still referring to FIG. 2, an exemplary interface module 20 may include an enclosure 26. The enclosure 26 may be detachable for cleaning and/or sterilization of the internal parts of the interface module 20. Within the enclosure 26 is contained an outlet valve or first valve 28 in a first flowpath 30 and an exhaust valve or second valve 32 in a second flowpath 34.

The first flowpath 30 communicates with the internal gas tank 48 via line 72 and with the housing outlet 22 of the interface module 20, which is pneumatically connected to the housing 14 of the filter device 12 via line 16. The first flowpath 30 may include a section 31, which may be vertical with respect to the flowpath 72 leading from the internal gas tank 48. The vertical section 31 may help prevent potential liquid ingress from the filter device 12 to the testing device 40. In some embodiments, a check valve 36 may be disposed in the vertical section 31. The check valve 36 may be configured to prevent any liquid flow in the direction from the filter device 12 to the testing device 40.

The second flowpath 34 communicates with the exhaust outlet 24 and the housing outlet 22 of the interface module 20. The second valve 32 in the second flowpath 34 and the first valve 28 in the first flowpath 30 may be pneumatically controlled. The pressure or reduced pressure for operation of the first and second valves 28 and 32 may be applied via lines 61 and 63 respectively and by controlling the outlet pilot valve 60 and the exhaust pilot valve 62 in the testing device 40, which in turn may be turned on or off by an electric current through a solenoid.

Advantageously, the interface module 20 may be attached to and detach from the testing device 40 via proper fittings. The interface module 20 may be removed from the testing device 40 for cleaning and/or sterilization. After the cleaning and/or sterilization, the interface module 20 may be re-attached to the testing device 40 for additional tests.

Referring to FIG. 2, in operation of the apparatus 10 for an integrity test on the filter device 12, a pressurized gas may be introduced to the housing 14 of the filter device 12 from the testing device 40 via the interface module 20. This may be accomplished by opening the isolation valve 58 on line 72 in the testing device 40, and by opening the first valve 28 in the first flowpath 30 and closing the second valve 32 in the second flowpath 34 in the interface module 20. The first valve 28 may be opened by e.g. turning on outlet pilot valve 60. The second valve 32 may be closed by e.g. turning off the exhaust pilot valve 62. After a desired pressure is established in the housing 14 of the filter device 12, an integrity test may be conducted in the manner known in the art.

In venting the filter device 12 after the integrity test, the pressurized gas or at least a portion of the pressurized gas in the housing 14 of the filter device 12 may be released or vented to an exhaust via the interface module 20. This may be accomplished by closing the first valve 28 in the first flowpath 30 and opening the second valve 32 in the second flowpath 34 in the interface module 20. The pressurized gas may be vented to the same classification area where the apparatus 10 is located. Alternatively, in case the pressurized gas contains any harmful contaminants, an elongate tube may be coupled to the exhaust outlet 24 to direct the gas to a different classification area. The use of the interface module 20, including a vertical flowpath section and/or a check valve in the flowpath, can advantageously prevent liquid ingress from the filter housing into the testing device, and as such, the risk of contamination of the testing device is reduced. To exhaust the testing device 40 during the test ending cycle, valve 28 may be opened after the pressure in the housing 14 is reduced to a desired low level as monitored by the transducer 70. Alternatively, valve 28 can be opened based on pressure decay time of the filter housing 14.

After the integrity test is completed and the system is de-energized, the interface module 20 may be disconnected and detached from the testing device 40. The interface module 20, including the valves and/or flowpaths, may be then cleaned using a suitable method such as wiping, flushing, and wet cleaning with a suitable cleaning agent. Alternatively, the interface module 20 or its components may be sterilized by e.g. subjecting the interface module or components to high pressure steam in an autoclave for a period of time. The cleaning and/or sterilization of the interface module may advantageously prevent cross-contamination from batch to batch or from product to product.

A testing apparatus and a method of testing the integrity of filter devices are described. Those skilled in the art will appreciate that various modifications may be made within the spirit and scope of the invention. For example, in some embodiments, the interface module 20 can be placed near the housing 14 of the filter device 12 by means of a fixture and extendable tubing connected to testing device 40. All these or other variations and modifications are contemplated by the inventors and within the scope of the invention.

What is claimed is:

1. A modular device for interfacing a testing device and a filter device, the modular device comprising:
   a first flowpath communicating with an outlet of a testing device and a housing of a filter device;
   a first valve disposed in the first flowpath;
   a second flowpath communicating with the housing of the filter device and an exhaust;
   a second valve disposed in the second flowpath; and
   an enclosure enclosing the first flowpath, the first valve, the second flowpath, and the second valve, wherein the modular device further comprises a first outlet configured to connect the first and second flowpaths with the housing of the filter device via an elongate tube, and a second outlet configured to connect the second flowpath to the exhaust.

2. The modular device of claim 1 wherein the first flowpath comprises a vertical section and the check valve is disposed in the vertical section.

3. The modular device of claim 1 wherein the first and/or second valves are pneumatically controllable.

4. The modular device of claim 1 wherein the modular device is cleanable and/or sterilizable.

5. The modular device of claim 1 further comprising fittings configured to removably attach the modular device to the testing device.

6. An apparatus, comprising:
   a testing device having an outlet for introducing a pressurized gas to a filter device, the filter device comprising a housing and a porous material to be tested; and
   an interface module removably attached to the testing device, the interface module comprising:
      a first flowpath communicating with the outlet of the testing device and the housing of the filter device;
      a first valve disposed in the first flowpath;
      a second flowpath communicating with the housing of the filter device and an exhaust;
      a second valve disposed in the second flowpath; and
      an enclosure enclosing the first flowpath, the first valve, the second flowpath, and the second valve, wherein the interface module further comprises a first outlet configured to connect the first and second flowpaths with the housing of the filter device via an elongate tube, and a second outlet configured to connect the second flowpath to the exhaust.

7. The apparatus of claim 6 wherein the testing device is configured to conduct one or more non-destructive tests on the filter device.

8. The apparatus of claim 6 wherein the interface module is cleanable and/or sterilizable.

9. The apparatus of claim 6 wherein the first and/or second valves of the interface module are pneumatically controllable.

10. The apparatus of claim 9 wherein the first and/or second valves of the interface module are controlled by the testing device.

11. The apparatus of claim 6 wherein the interface module further comprises a check valve in the first flowpath configured to prevent a liquid flow in a direction from the filter device to the testing device.

12. The apparatus of claim 11 wherein the first flowpath comprises a vertical section and the check valve is disposed in the vertical section.

13. The apparatus of claim 6 wherein the testing device comprises a pressure sensor or transducer configured to measure a pressure in the housing of the filter device.

14. A method of testing a filter device, comprising:
   connecting a testing device with a filter device via an interface module, wherein the interface module comprises:
      a first flowpath communicating with an outlet of the testing device and a housing of the filter device, a first valve in the first flowpath, a second flowpath communicating with the housing of the filter device and an exhaust, a second valve in the second flowpath, and an enclosure enclosing the first flowpath, the first valve, the second flowpath, and the second valve; and
   conducting an integrity test on the filter device, wherein
      a pressurized gas is introduced from the testing device to the housing of the filter device via the first flowpath of the interface module; and
      at least a portion of the pressurized gas in the filter device is vented to the exhaust via the second flowpath of the interface module.

15. The method of claim 14 wherein in introducing the pressurized gas to the housing of the filter device, the first valve in the first flowpath is pneumatically opened, and the second valve in the second flowpath is pneumatically closed, and wherein in venting the portion of the pressurized gas in the filter device, the second valve in the second flowpath is pneumatically opened, and the first valve in the first flowpath is pneumatically closed.

16. The method of claim 14 wherein the interface module is removably attached to the testing device.

17. The method of claim 16 further comprising removing the interface module from the testing device and subsequently cleaning and/or sterilizing the interface module.

18. The method of claim 14 wherein the integrity test comprises a non-destructive test on the filter device.

19. The method of claim 14 further comprising the step of venting the testing device after the integrity test, wherein the first valve in the first flowpath is pneumatically opened in venting the testing device.

* * * * *